(12) United States Patent
Viker

(10) Patent No.: US 8,252,025 B2
(45) Date of Patent: Aug. 28, 2012

(54) VERTEBRAL FIXATION SYSTEM

(75) Inventor: Thomas O. Viker, Arden Hills, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 750 days.

(21) Appl. No.: 12/203,664

(22) Filed: Sep. 3, 2008

(65) Prior Publication Data

US 2010/0057125 A1    Mar. 4, 2010

(51) Int. Cl.
*A61B 17/70* (2006.01)

(52) U.S. Cl. ......... 606/246; 606/255; 606/266; 606/278

(58) Field of Classification Search .......... 606/246–279; 403/76–77
See application file for complete search history.

(56) References Cited

U.S. PATENT DOCUMENTS

| | | | | |
|---|---|---|---|---|
| 5,540,688 | A * | 7/1996 | Navas | 606/266 |
| 6,802,844 | B2 * | 10/2004 | Ferree | 606/258 |
| 7,846,186 | B2 * | 12/2010 | Taylor | 606/249 |
| 2002/0035365 | A1 * | 3/2002 | Kumar et al. | 606/61 |
| 2002/0133155 | A1 * | 9/2002 | Ferree | 606/61 |
| 2004/0254577 | A1 * | 12/2004 | Delecrin et al. | 606/61 |
| 2005/0171537 | A1 * | 8/2005 | Mazel et al. | 606/61 |
| 2006/0064090 | A1 | 3/2006 | Park | |
| 2007/0225708 | A1 * | 9/2007 | Biedermann et al. | 606/61 |
| 2008/0039843 | A1 | 2/2008 | Abdou | |
| 2008/0071275 | A1 * | 3/2008 | Ferree | 606/61 |
| 2008/0183215 | A1 | 7/2008 | Altarac et al. | |
| 2010/0228292 | A1 * | 9/2010 | Arnold et al. | 606/264 |

FOREIGN PATENT DOCUMENTS

| | | |
|---|---|---|
| DE | 29818831 U1 | 12/1998 |
| DE | 100117426 A1 | 10/2002 |
| DE | 202007009970 U1 | 9/2007 |
| EP | 1800614 A1 | 6/2007 |
| FR | 2846223 A1 | 4/2004 |
| WO | 2005110257 A1 | 11/2005 |
| WO | 2007014119 A2 | 2/2007 |
| WO | 2008013892 A2 | 1/2008 |
| WO | 2008021319 A2 | 2/2008 |
| WO | 2008/027332 A2 | 3/2008 |
| WO | 2008034130 A2 | 3/2008 |

\* cited by examiner

*Primary Examiner* — Eduardo C Robert
*Assistant Examiner* — Stuart S Bray
(74) *Attorney, Agent, or Firm* — Seager Tufte & Wickhem LLC

(57) ABSTRACT

A vertebral stabilization assembly for stabilizing a vertebral segment. The assembly includes a vertebral anchor, a first stabilization member, a second stabilization member, and a threaded fastener. A post of the first stabilization member is configured to be positioned in a first socket of the head portion of the vertebral anchor and a post of the second stabilization member is configured to be positioned in a second socket of the head portion of the vertebral anchor. The threaded fastener is configured to threadedly engage a threaded opening of the head portion such that when the threaded fastener is threaded into the threaded opening, the threaded fastener engages both the post of the first stabilization member and the post of the second stabilization member.

29 Claims, 18 Drawing Sheets

VERTEBRAL FIXATION SYSTEM

TECHNICAL FIELD

The disclosure is directed to a vertebral fixation system for stabilizing a spinal segment. More particularly, the disclosure is directed to vertebral anchors having sockets for receiving posts of connecting members.

BACKGROUND

The spinal column of a patient includes a plurality of vertebrae linked to one another by facet joints and an intervertebral disc located between adjacent vertebrae. The facet joints and intervertebral disc allow one vertebra to move relative to an adjacent vertebra, providing the spinal column a range of motion. Diseased, degenerated, damaged, or otherwise impaired facet joints and/or intervertebral discs may cause the patient to experience pain or discomfort and/or loss of motion, thus prompting surgery to alleviate the pain and/or restore motion of the spinal column.

Accordingly, there is an ongoing need to provide alternative apparatus, devices, assemblies, systems and/or methods that can function to alleviate pain or discomfort, provide stability, such as dynamic stability, and/or restore a range of motion to a spinal segment of a spinal column.

SUMMARY

The disclosure is directed to several alternative designs, materials and methods of manufacturing and using vertebral fixation systems and components to provide a degree of stability to a vertebral segment of a spinal column.

Accordingly, one illustrative embodiment is a vertebral stabilization assembly including a vertebral anchor, a first stabilization member, a second stabilization member, and a threaded fastener. The vertebral anchor includes a head portion and a bone engagement portion extending from the head portion. The head portion includes a first socket and a second socket. The first stabilization member includes a post located at a first end of the first stabilization member, and the second stabilization member includes a post located at a first end of the second stabilization member. The post of the first stabilization member is configured to be positioned in the first socket and the post of the second stabilization member is configured to be positioned in the second socket. The threaded fastener is configured to threadedly engage a threaded opening of the head portion. When the threaded fastener is threaded into the threaded opening, the threaded fastener engages both the post of the first stabilization member and the post of the second stabilization member.

Another illustrative embodiment is a vertebral stabilization assembly including a first vertebral anchor, a second vertebral anchor, and a connector extendable between the first vertebral anchor and the second vertebral anchor. The first vertebral anchor includes head portion and a bone engagement portion extending from the head portion along a longitudinal axis of the first vertebral anchor. The head portion of the first vertebral anchor includes a socket. The second vertebral anchor includes a head portion and a bone engagement portion extending from the head portion along a longitudinal axis of the second vertebral anchor. The connector includes a spacer, an elongate member extending through the spacer, and a first post secured to the elongate member. The first post is configured to be inserted into the socket of the first vertebral anchor. The elongate member is placed in tension as the first post is inserted into the socket of the first vertebral anchor in a direction generally parallel with the longitudinal axis of the first vertebral anchor.

Another illustrative embodiment is a vertebral anchor including a head portion and a shaft portion extending from the head portion and defining a longitudinal axis. The head portion includes a first socket, a second socket, a first side opening providing access to the first socket from a first side of the head portion, and a second side opening providing access to the second socket from a second side of the head portion. The first socket includes a side wall which tapers toward the longitudinal axis from an upper portion of the first socket toward a lower portion of the first socket, and the second socket includes a side wall which tapers toward the longitudinal axis from an upper portion of the second socket toward a lower portion of the second socket. The vertebral anchor may include a threaded fastener configured to threadedly engage with the head portion. The threaded fastener may be configured to extend across a portion of the first socket and extend across a portion of the second socket.

Another illustrative embodiment is a vertebral anchor including a head portion and a shaft portion extending from the head portion and defining a longitudinal axis of the vertebral anchor. The head portion includes a first cylindrical bore extending into the head portion such that the central longitudinal axis of the first cylindrical bore is at an oblique (e.g., acute) angle to the longitudinal axis of the vertebral anchor. The head portion also includes a second cylindrical bore extending into the head portion such that the central longitudinal axis of the second cylindrical bore is at an oblique (e.g., acute) angle to the longitudinal axis of the vertebral anchor. The head portion further includes a first side opening providing access to the first cylindrical bore from a first side of the head portion and a second side opening providing access to the second cylindrical bore from a second side of the head portion. The head portion also includes a threaded opening extending into the head portion from an upper surface of the head portion configured to receive a threaded fastener. The threaded opening intersects both the first cylindrical bore and the second cylindrical bore.

Another illustrative embodiment is a method of manufacturing a vertebral anchor having a head portion and a shaft portion extending along a longitudinal axis of the vertebral anchor. The method includes forming a first bore, a second bore and a threaded bore into the head portion. The first bore has a longitudinal axis extending at an oblique (e.g., acute) angle to the longitudinal axis of the vertebral anchor. The second bore has a longitudinal axis extending at an oblique (e.g., acute) angle to the longitudinal axis of the vertebral anchor. The threaded bore, which is configured to receive a threaded fastener, intersects both the first bore and the second bore.

Yet another illustrative embodiment is a method of stabilizing a vertebral segment of a spinal column. A vertebral anchor is secured to a vertebra of the spinal column. The vertebral anchor includes a head portion and a shaft portion extending from the head portion. The head portion includes a first socket and a second socket. The post of a first stabilization member is positioned in the first socket and the post of a second stabilization member is positioned in the second socket. With a single fastener, the post of the first stabilization member is secured in the first socket and the post of the second stabilization member is secured in the second socket. As the single fastener is securing the posts, the post of the first stabilization member moves toward the post of the second stabilization member.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which.

Figure 1:
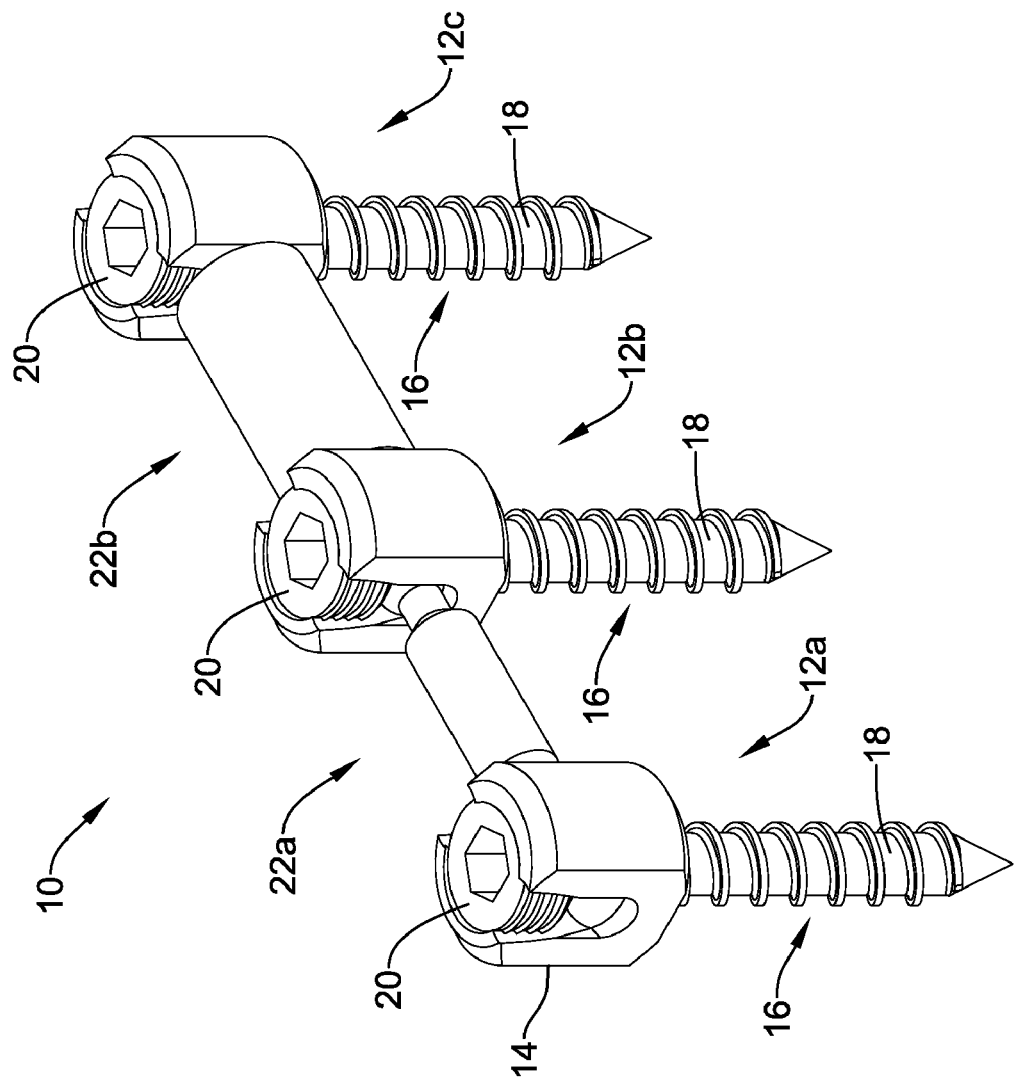
FIG. 1 is a perspective view of an exemplary vertebral stabilization assembly for stabilizing a vertebral segment.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Referring to FIG. 1, there is shown a vertebral stabilization assembly 10 for stabilizing a portion of a spinal column, such as one or more spinal segments of a spinal column. As used herein, a spinal segment is intended to refer to two or more vertebrae, the intervertebral disc(s) between the vertebrae and other anatomical elements between the vertebrae. For example, a spinal segment may include first and second adjacent vertebrae and the intervertebral disc located between the first and second vertebrae. In some embodiments the vertebral stabilization assembly 10 may provide rigid support to the spinal segment. In other embodiments, the vertebral stabilization assembly 10 may offer flexible support to the spinal segment in torsion, lateral bending, extension and/or flexion. In some embodiments, the vertebral stabilization assembly 10 may help preserve the facet joints between adjacent vertebrae by providing facet offloading and/or may stabilize or reverse neural foraminal narrowing of the spinal column. Thus, in some embodiments, the spinal stabilization assembly 10 may provide rigid stabilization to a spinal segment, while in other embodiments the spinal stabilization assembly 10 may provide dynamic stabilization to a spinal segment, preserving and/or allowing for a range of motion of the spinal segment.

In some embodiments, the vertebral stabilization assembly 10 may be used to treat discogenic low back pain, degenerative spinal stenosis, disc herniations, facet syndrome, posterior element instability, adjacent level syndrome associated with spinal fusion, and/or other maladies associated with the spinal column.

The vertebral stabilization assembly 10 may include one or more or a plurality of vertebral anchors or fasteners 12. Although the vertebral anchors 12 are depicted as threaded vertebral fasteners (e.g., pedicle screws, bone screws), in some embodiments the vertebral anchors 12 may be vertebral hooks (e.g., laminar hooks) or other types of fastening members for attachment to a bony structure such as a vertebra of the spinal column. Each of the vertebral anchors 12 may be configured to be secured to a vertebra of a spinal column. For instance, the first vertebral anchor 12a may be secured to a first vertebra, the second vertebral anchor 12b may be secured to a second vertebra, and the third vertebral anchor 12c may be secured to a third vertebra.

The vertebral anchor 12 may include a head portion 14 and a bone engagement portion 16 extending from the head portion 14. In some embodiments, the bone engagement portion 16 may be a shaft portion 18 of the vertebral anchor 12 extending from the head portion 14 along a longitudinal axis of the vertebral anchor 12. In some embodiments, the vertebral anchor 12 may be a monoaxial screw, and in other embodiments the vertebral anchor 12 may be a polyaxial screw. In some embodiments, the shaft portion 18 may be configured to be installed into a bony region of a vertebra of the spinal column. For example, the shaft portion 18 may be installed into a pedicle of a vertebra, or other region of a vertebra. In some embodiments, the shaft portion 18 may be a threaded region having helical threads configured to be screwed into a pedicle of a vertebra, or other bony region of a vertebra.

The vertebral anchor 12 may include a securing element, such as a threaded fastener 20 (e.g., a set screw, cap) configured to engage the head portion 14 to secure a stabilizing member or connecting member 22 to the vertebral anchor 12. For example, the threaded fastener 20 may include threads which mate with threads formed in the head portion 14.

The vertebral stabilization assembly 10 may also include one or more, or a plurality of stabilization members or connecting members 22 extending between vertebral anchors 12 of the vertebral stabilization assembly 10. As an illustrative example, the vertebral stabilization assembly 10 shown in FIG. 1 includes a first connecting member 22a extending between and secured to the first vertebral anchor 12a and the second vertebral anchor 12b, and a second connecting member 22b extending between and secured to the second vertebral anchor 12b and the third vertebral anchor 12c. The connecting members 22 will be further discussed later herein.

Figure 2:
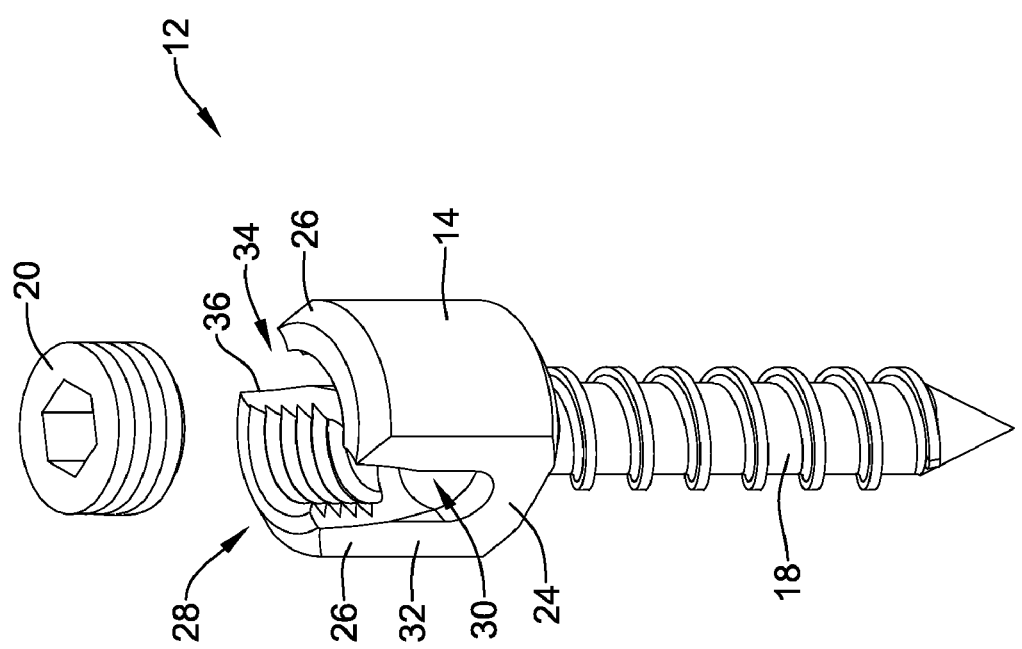
FIG. 2 is a perspective view of one embodiment of a vertebral anchor which may be used in the vertebral stabilization assembly of FIG. 1.
Figure 3:
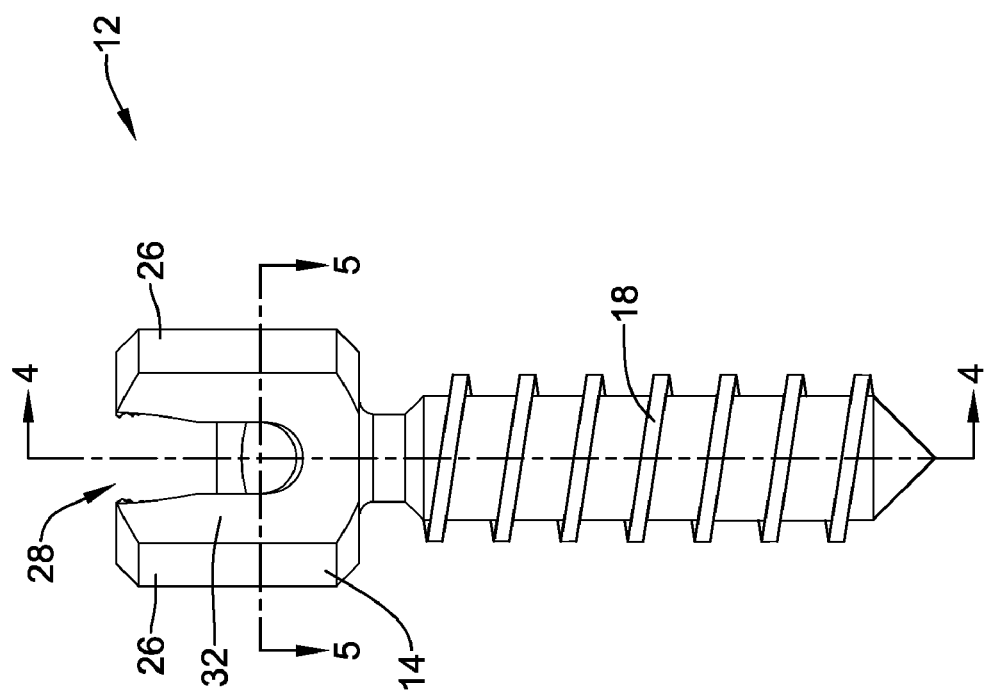
FIG. 3 is a plan view of the vertebral anchor of FIG. 2.

Referring to FIGS. 2 and 3, there is shown a vertebral anchor 12 of the vertebral stabilization assembly 10. The head portion 14 may include a base portion 24, from which the shaft portion 18 extends from, and first and second legs 26 extending from the base portion 24 on opposing sides of the head portion 14. The first and second legs 26 may define a threaded opening 28 extending into the head portion 14 from an upper extent of the head portion 14 opposite the base portion 24. Each of the first and second legs 26 may include a threaded portion for threadedly engaging a threaded portion of the threaded fastener 20.

The head portion 14 may additionally include a first side opening 30 extending into the head portion 14 from a first side surface 32 of the head portion. Furthermore, the head portion 14 may include a second side opening 34 extending into the head portion 14 from a second side surface 36 of the head portion, opposite the first side surface 32. The first side opening 30 may intersect and/or be in communication with a first socket (shown in FIG. 4) of the head portion 14, and the second side opening 34 may intersect and/or be in communication with a second socket (shown in FIG. 4) of the head portion 14.

Figure 4:
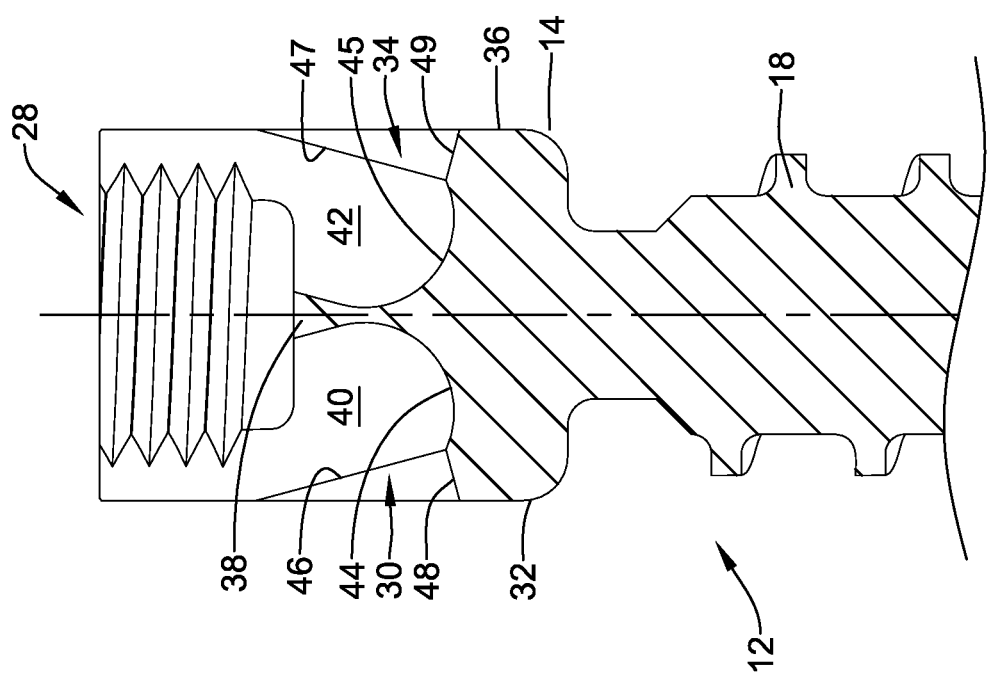
FIG. 4 is a longitudinal cross-sectional view of the vertebral anchor of FIG. 3 taken along line 4-4.

FIG. 4 is a longitudinal cross-sectional view of the vertebral anchor 12 shown in FIG. 3 taken along line 4-4. As shown in FIG. 4, the head portion 14 may include a first socket 40 and a second socket 42. The first socket 40 may be separated from the second socket 42 by a partition 38. Additionally, FIG. 4 illustrates the first side opening 30 intersecting and in communication with the first socket 40 and the second side opening 34 intersecting and in communication with the second socket 42. Furthermore, FIG. 4 illustrates the threaded opening 28 intersecting and in communication with each of the first socket 40 and the second socket 42 of the head portion 14 of the vertebral anchor 12.

The first socket 40 may include a tapered side surface 46 tapering toward the longitudinal axis of the vertebral anchor 12 from an upper portion of the first socket 40 toward a lower portion of the first socket 40. In some embodiments, the tapered side surface 46 may be oriented at about 5° to about 60°, about 10° to about 45°, or about 10° to about 30° to the longitudinal axis of the vertebral anchor 12. The tapered side surface 46 may be oriented at about 5°, about 10°, about 15°, about 20°, about 25°, about 30°, about 35°, about 40°, about 45°, about 50°, about 55° or about 60° to the longitudinal axis of the vertebral anchor 12 in some instances. In some embodiments, the tapered side surface 46 may be a concave surface. Additionally or alternatively, the second socket 42 may include a tapered side surface 47 tapering toward the longitudinal axis of the vertebral anchor 12 from an upper portion of the second socket 42 toward a lower portion of the second socket 42. In some embodiments, the tapered side surface 47 may be oriented at about 5° to about 60°, about 10° to about 45°, or about 10° to about 30° to the longitudinal axis of the vertebral anchor 12. The tapered side surface 47 may be oriented at about 5°, about 10°, about 15°, about 20°, about 25°, about 30°, about 35°, about 40°, about 45°, about 50°, about 55° or about 60° to the longitudinal axis of the vertebral anchor 12 in some instances. In some embodiments, the tapered side surface 47 may be a concave surface. Each of the first socket 40 and second socket 42 may also include a spherical end surface 44, 45, respectively, having a concave surface.

The first side opening 30, extending into the head portion 14 from the first side surface 32 of the head portion 14 may define a surface 48 extending from the first side surface 32 to the first socket 40. The surface 48 may be a concave surface in some instances. In some embodiments, the surface 48 may extend perpendicular to the longitudinal axis of the vertebral anchor 12. In other embodiments, the surface 48 may extend at an oblique angle to the longitudinal axis of the vertebral anchor 12. For example, in some embodiments the surface 48 may extend at about 45° to about 90°, about 60° to about 90°, about 60° to about 85°, or about 70° to about 80°. The surface 48 may extend at about 45°, about 50°, about 55°, about 60°, about 65°, about 70°, about 75°, about 80°, about 85°, or about 90° from the longitudinal axis of the vertebral anchor 12 in some instances.

The second side opening 34, extending into the head portion 14 from the second side surface 36 of the head portion 14 may define a surface 49 extending from the second side surface 36 to the second socket 42. The surface 49 may be a concave surface in some instances. In some embodiments, the surface 49 may extend perpendicular to the longitudinal axis of the vertebral anchor 12. In other embodiments, the surface 49 may extend at an oblique angle to the longitudinal axis of the vertebral anchor 12. For example, in some embodiments the surface 49 may extend at about 45° to about 90°, about 60° to about 90°, about 60° to about 85°, or about 70° to about 80°. The surface 49 may extend at about 45°, about 50°, about 55°, about 60°, about 65°, about 70°, about 75°, about 80°, about 85°, or about 90° from the longitudinal axis of the vertebral anchor 12 in some instances.

As shown in FIG. 4, the head portion 14 and the shaft portion 18 of the vertebral anchor 12 may be formed as a monolithic or unitary construction in some embodiments, or otherwise rigidly secured to one another. Thus, in such embodiments the head portion 14 is maintained at a single axial orientation relative to the shaft portion 18 along the longitudinal axis of the vertebral anchor 12. In other embodiments, the head portion 14 may be coupled to the shaft portion 18 in a manner that allows for polyaxial orientation of the head portion 14 relative to the shaft portion 18 and the longitudinal axis of the vertebral anchor 12 at one of a plurality of angular positions relative to the longitudinal axis of the vertebral anchor 12.

Figure 5:
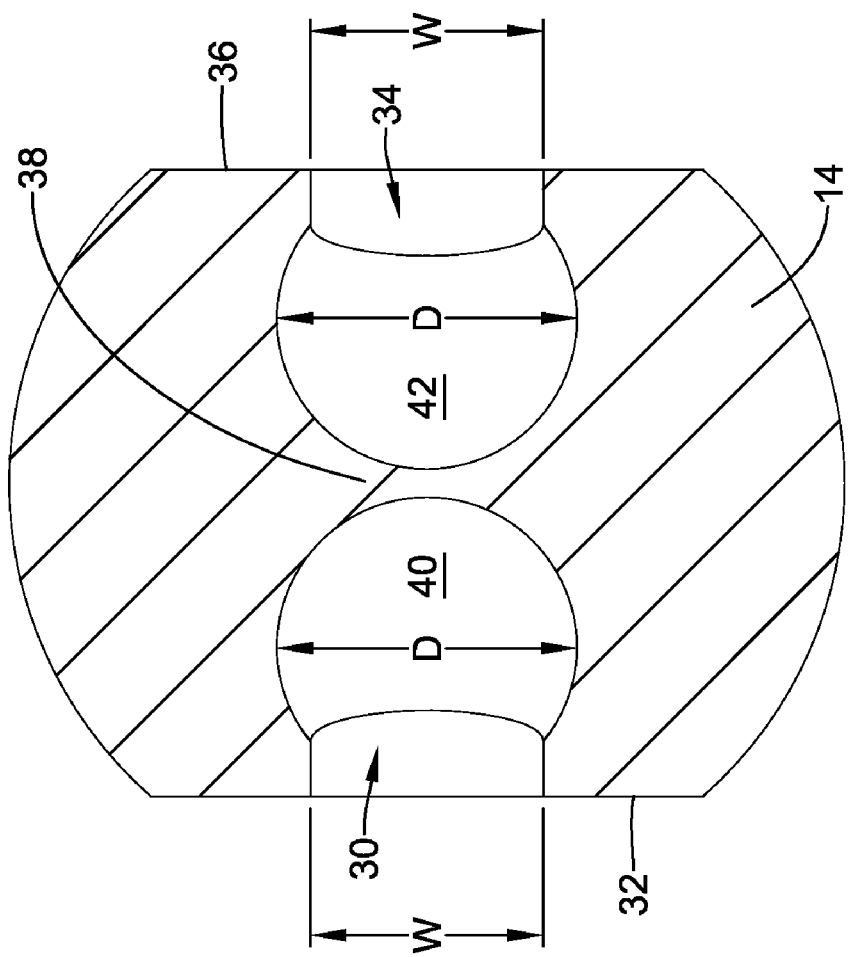
FIG. 5 is a transverse cross-sectional view of the vertebral anchor of FIG. 3 taken along line 5-5.

FIG. 5 is a transverse cross-sectional view of the vertebral anchor 12 shown in FIG. 3 taken along line 5-5. As shown in FIG. 5, the head portion 14 of the vertebral anchor 12 includes a first socket 40 and a second socket 42. The first socket 40 is shown separated from the second socket 42 by the partition 38 located between the first socket 40 and the second socket 42. Additionally, the first side opening 30 is shown extending from the first side surface 32 of the head portion 14 to the first socket 40, such that the first side opening 30 intersects and is in communication with the first socket 40. The second side opening 34 is also shown extending from the second side surface 36 of the head portion 14 to the second socket 42, such that the second side opening 34 intersects and is in communication with the second socket 42.

The first socket 40 and the second socket 42, which may be cylindrical sockets in some instances, may have a diameter D, or other cross-sectional dimension. The diameter D of the first socket 40 may be the same as the diameter D of the second socket 42 in some embodiments, while in other embodiments the diameter D of the first socket 40 may be different from the diameter D of the second socket 42.

The first side opening 30 may have a width W less than the diameter D of the first socket 40. As will be discussed further herein, a post of a connector 22 may be positioned in the first socket 40 from the upper portion of the head portion 14 (i.e., top loaded). When the post of the connector 22 which has a cross-sectional dimension (e.g., diameter) greater than the width W of the first side opening 30 and less than the diameter D of the first socket 40 (albeit slightly less in some instances) is positioned in the first socket 40, the post of the connector 22 will be prevented from being removed from the head portion 14 in a lateral direction generally perpendicular to the longitudinal axis of the vertebral anchor 12. Furthermore, the second side opening 34 may have a width W less than the diameter D of the second socket 42. A post of a connector 22 may be positioned in the second socket 42 from the upper portion of the head portion 14 (i.e., top loaded). When the post of the connector 22 which has a cross-sectional dimension (e.g., diameter) greater than the width W of the second side opening 34 and less than the diameter D of the second socket 42 (albeit slightly less in some instances) is positioned in the second socket 42, the post of the connector 22 will be prevented from being removed from the head portion 14 in a lateral direction generally perpendicular to the longitudinal axis of the vertebral anchor 12.

Figure 6A:
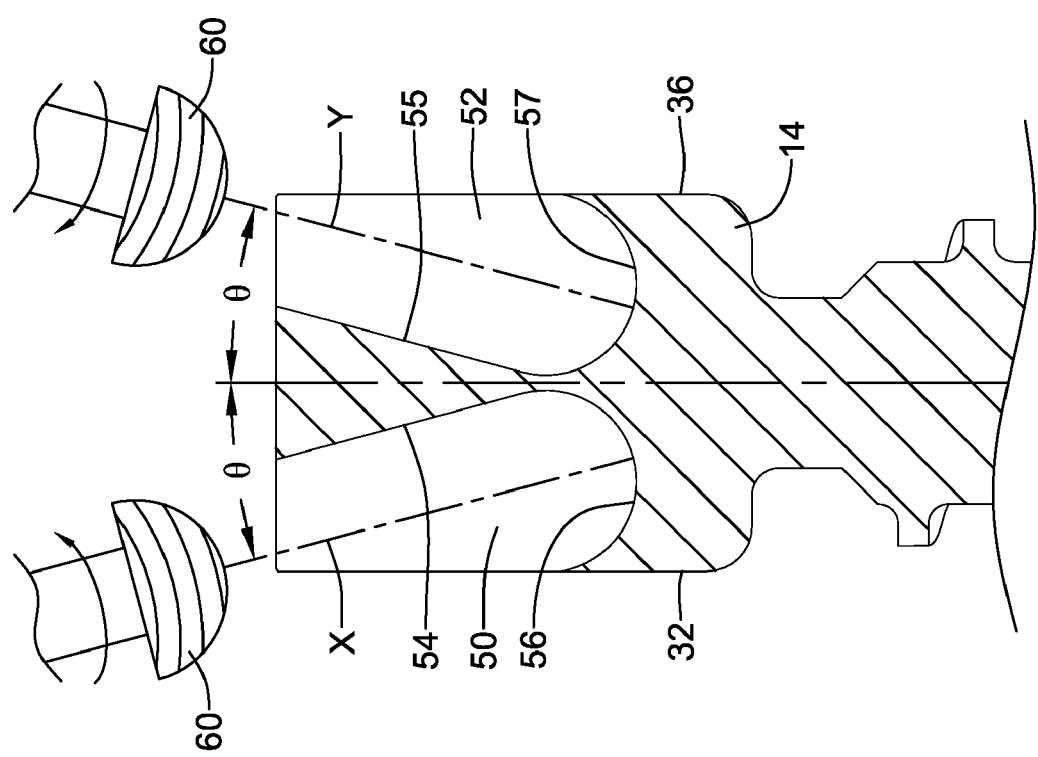
FIG. 6A-6C illustrate one possible method of manufacturing the head portion of the vertebral anchor of FIG. 2.
Figure 6B:
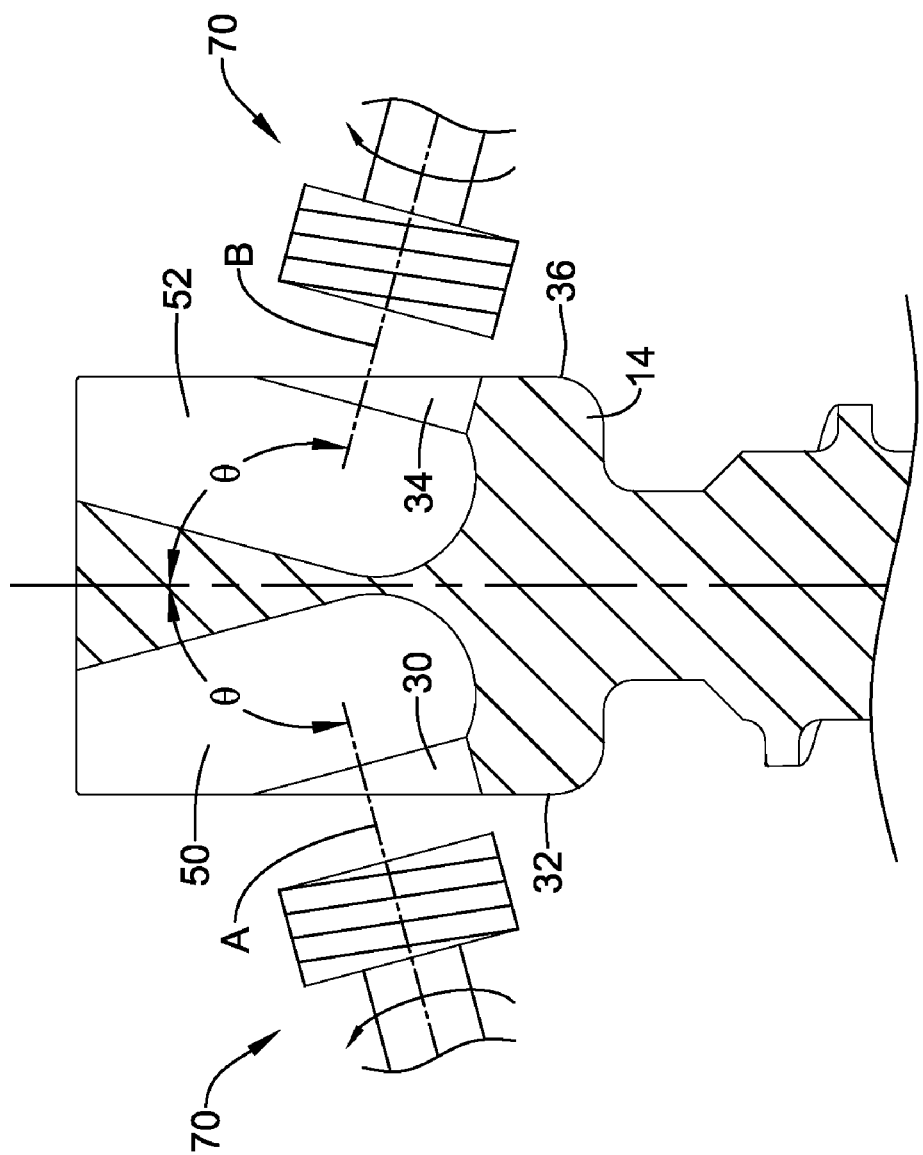
Figure 6C:
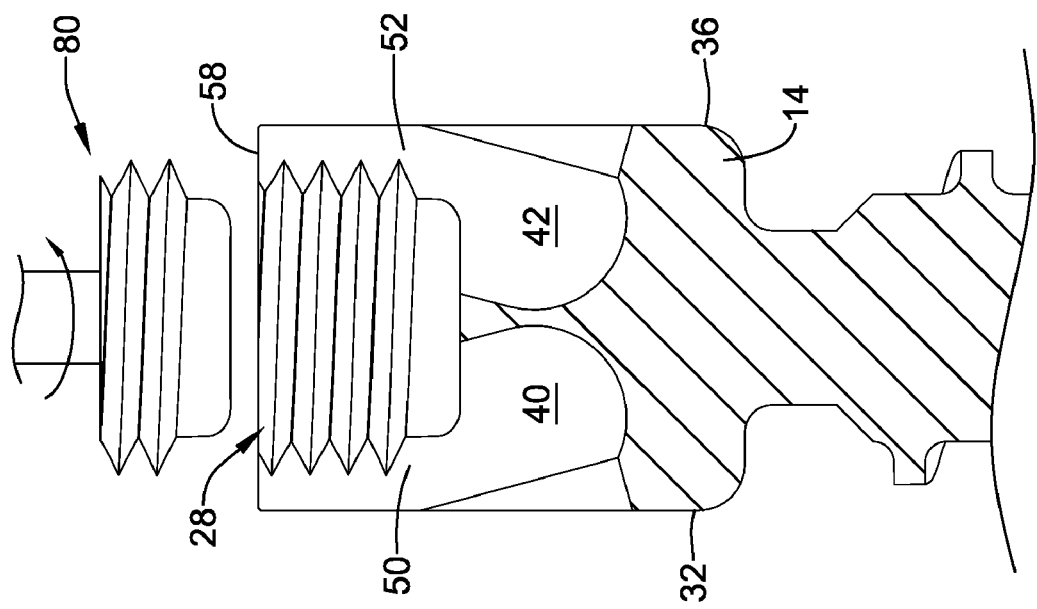

FIGS. 6A through 6C illustrate one possible method of manufacturing the head portion 14 of the vertebral anchor 12 to include the first socket 40 and the second socket 42. As shown in FIG. 6A, to form the first and second sockets 40, 42, a cutting tool, such as an endmill, may be used to form a first bore 50 and a second bore 52 in the head portion 14. In some instances a ball endmill 60 may be used to form the first bore 50 and the second bore 52. By using a ball endmill 60, each of the first bore 50 and the second bore 52 may be formed to have a cylindrical side wall 54, 55, respectively, and a spherical end wall 56, 57, respectively. The first and second bores 50, 52 may define, at least in part, the first and second sockets 40, 42, respectively, of the head portion 14 of the vertebral anchor 12.

The ball endmill 60 may be advanced into the head portion 14 while being rotated at a high rotational speed to bore out the first bore 50 and the second bore 52. The ball endmill 60 may be advanced or translated into the head portion 14 along a first axis X to form the first bore 50. Thus, the first axis X defines a longitudinal axis of the first bore 50. The first axis X may be at an oblique angle to the longitudinal axis of the vertebral anchor 12. In some embodiments, the first axis X may extend at an angle of about 5° to about 60°, about 10° to about 45°, or about 10° to about 30° to the longitudinal axis of the vertebral anchor 12. For example, the first axis X may extend at an angle of about 5°, about 10°, about 15°, about 20°, about 25°, about 30°, about 35°, about 40°, about 45°, about 50°, about 55° or about 60° to the longitudinal axis of the vertebral anchor 12 in some instances. In other embodiments, the ball endmill 60 may be advanced into the head portion 14 along an arcuate pathway to form an arcuate first bore 50.

Furthermore, the ball endmill 60 may be advanced or translated into the head portion 14 along a second axis Y to form the second bore 52. Thus, the second axis Y defines a longitudinal axis of the second bore 52. The second axis Y may be at an oblique angle to the longitudinal axis of the vertebral anchor 12. In some embodiments, the second axis Y may extend at an angle of about 5° to about 60°, about 10° to about 45°, or about 10° to about 30° to the longitudinal axis of the vertebral anchor 12. For example, the second axis Y may extend at an angle of about 5°, about 10°, about 15°, about 20°, about 25°, about 30°, about 35°, about 40°, about 45°, about 50°, about 55° or about 60° to the longitudinal axis of the vertebral anchor 12 in some instances. In other embodiments, the ball endmill 60 may be advanced into the head portion 14 along an arcuate pathway to form an arcuate second bore 52.

Additionally, as shown in FIG. 6B, a cutting tool, such as an endmill 70, may be used to form the first and second side openings 30, 34 extending into the interior of the head portion 14 from the first and second side surfaces 32, 36, respectively. The endmill 70 may be advanced into the head portion 14 while being rotated at a high rotational speed to bore out the first side opening 30 and the second side opening 34. The endmill 70 may be advanced or translated into the head portion 14 along a first axis A to form the first side opening 30. The first axis A may be at an oblique angle or a perpendicular angle to the longitudinal axis of the vertebral anchor 12. In some embodiments, the first axis A may extend at an angle of about 45° to about 90°, about 60° to about 90°, about 60° to about 85°, or about 70° to about 80° to the longitudinal axis of the vertebral anchor 12. For example, the first axis A may extend at an angle of about 45°, about 50°, about 55°, about 60°, about 65°, about 70°, about 75°, about 80°, about 85°, or about 90° to the longitudinal axis of the vertebral anchor 12 in some instances.

Furthermore, the endmill 70 may be advanced or translated into the head portion 14 along a second axis B to form the second side opening 34. The second axis B may be at an oblique angle or a perpendicular angle to the longitudinal axis of the vertebral anchor 12. In some embodiments, the second axis B may extend at an angle of about 45° to about 90°, about 60° to about 90°, about 60° to about 85°, or about 70° to about 80° to the longitudinal axis of the vertebral anchor 12. For example, the second axis B may extend at an angle of about 45°, about 50°, about 55°, about 60°, about 65°, about 70°, about 75°, about 80°, about 85°, or about 90° to the longitudinal axis of the vertebral anchor 12 in some instances.

Forming the first and second side openings 30, 34 may allow a portion of a first connector 22 to extend through the first side opening 30 to the first socket 40 and may allow a portion of a second connector 22 to extend through the second side opening 34 to the second socket 42. Thus, as discussed further herein, a post of a first connector 22 may be positioned in the first socket 40 while a portion of the first connector 22 extending from the post passes through the first side opening 30 to exterior of the head portion 14. Similarly, a post of a second connector 22 may be positioned in the second socket 42 while a portion of the second connector 22 extending from the post passes through the second side opening 34 to exterior of the head portion 14 on an opposite side of the head portion 14.

As shown in FIG. 6C, an opening, such as a threaded opening 28, may be formed into the head portion 14 from an upper surface 58 of the head portion 14. For example, a cutting device may form a bore into the head portion 14 from the upper surface 58, and then a tap 80 may be used to form internal threads in the formed bore to create the threaded opening 28. In other embodiments, the threaded opening 28 may be formed with one or more other techniques. The threaded opening 28 may intersect and be in communication with each of the first bore 50 (at least partially defining the first socket 40) and the second bore 52 (at least partially defining the second socket 42). The threaded opening 28 may be configured to threadedly receive a threaded fastener 20, such as a set screw, therein.

Figure 7:
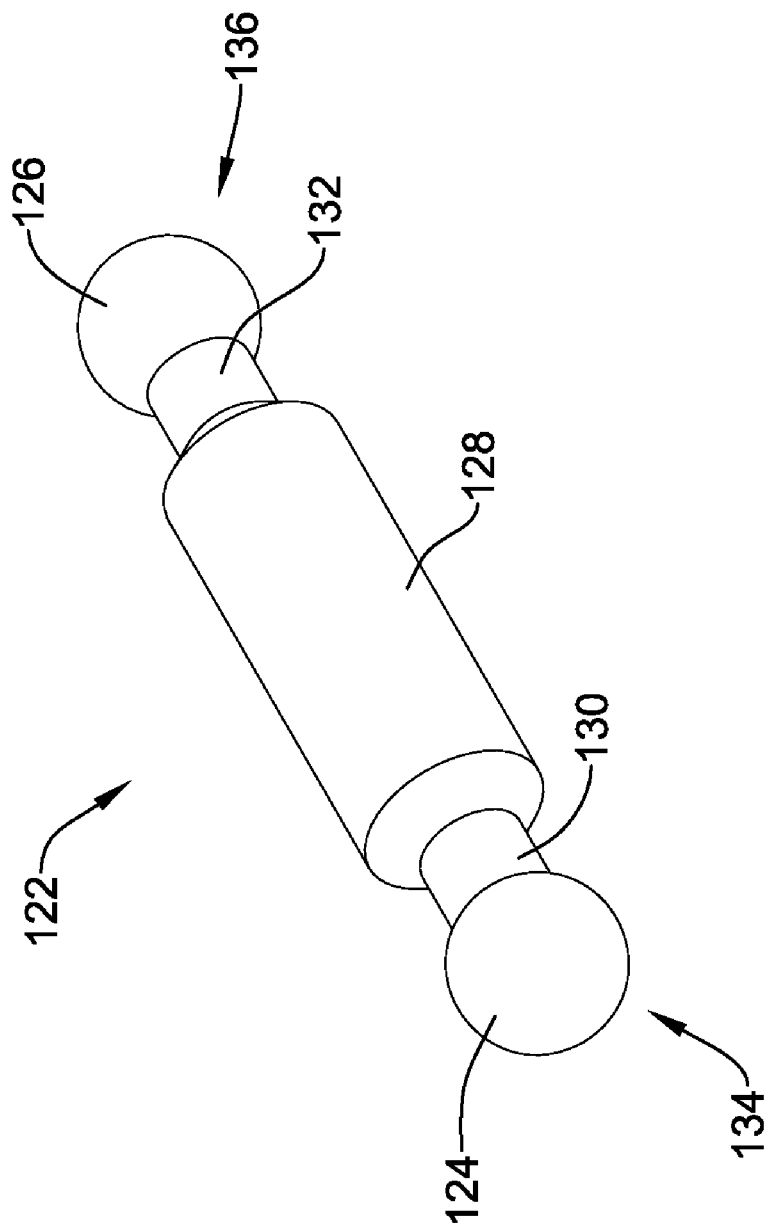
FIG. 7 is a perspective view of an exemplary connector which may be used in stabilizing a vertebral segment.

Some possible configurations of connectors configured to extend between a first vertebral anchor 12 and a second vertebral anchor 12 will now be further described. One illustrative embodiment of a connector 122 is shown in FIG. 7. The connector 122, which may be formed of a monolithic or unitary construction in some instances, may be a solid connector formed of a desired material. In some embodiments the connector 122 may be formed of a metallic material, a polymeric material, or combinations of these materials. Some suitable materials include stainless steel, nickel-titanium alloy, shape-memory alloy, titanium, polymers (e.g., polyetheretherketone (PEEK), polyethyleneterephthalate (PET)), polycarbonate urethane (PCU), or other suitable material. In some embodiments, the polymeric material may be reinforced with fibers or filaments, such as liquid crystal polymer (LCP) fibers or carbon fibers.

In some embodiments the connector 122 may be substantially incompressible and/or substantially non-distensible (e.g., not readily elongated or stretched). In other embodiments the connector 122 may be compressible, allowing for a degree of compressibility and/or may be distensible, allowing for a degree of elongation. In some embodiments the connector 122 may be considered a rigid or semi-rigid connector, providing a rigid or semi-rigid connection between a first vertebral anchor 12 and a second vertebral anchor 12.

The connector 122 may include a first post 124 proximate a first end 134 of the connector 122 and a second post 126 proximate a second end 136 of the connector 122. As shown in FIG. 7, in some embodiments the first post 124 and/or the second post 126 may be a substantially spherical ball. However, in other embodiments the first post 124 and/or the second post 126 may be formed to have a different shape, such as a wedge shape, a polygonal shape, or a ovoid shape, if desired.

The connector 122 may also include a central portion 128 located between the first post 124 and the second post 126. As shown in FIG. 7, in some embodiments the central portion 128 may have a cylindrical shape. However, in other embodiments the central portion 128 may have a different shape, if desired. In some embodiments, the central portion 128 may include one or more, or a plurality of features providing a degree of flexibility to the central portion 128. For instance, the central portion 128 may include one or more cuts, grooves, notches, ridges, and/or slots, providing the central portion 128 with desired flexibility characteristics.

The connector 122 may also include a first neck 130 extending between the first post 124 and the central portion 128 and a second neck 132 extending between the second post 126 and the central portion 128. The first neck 130 and/or the second neck 132 may have a smaller cross-sectional dimension (e.g., diameter) than at least a portion of the post 124, 126 and central portion 128.

Figure 8:
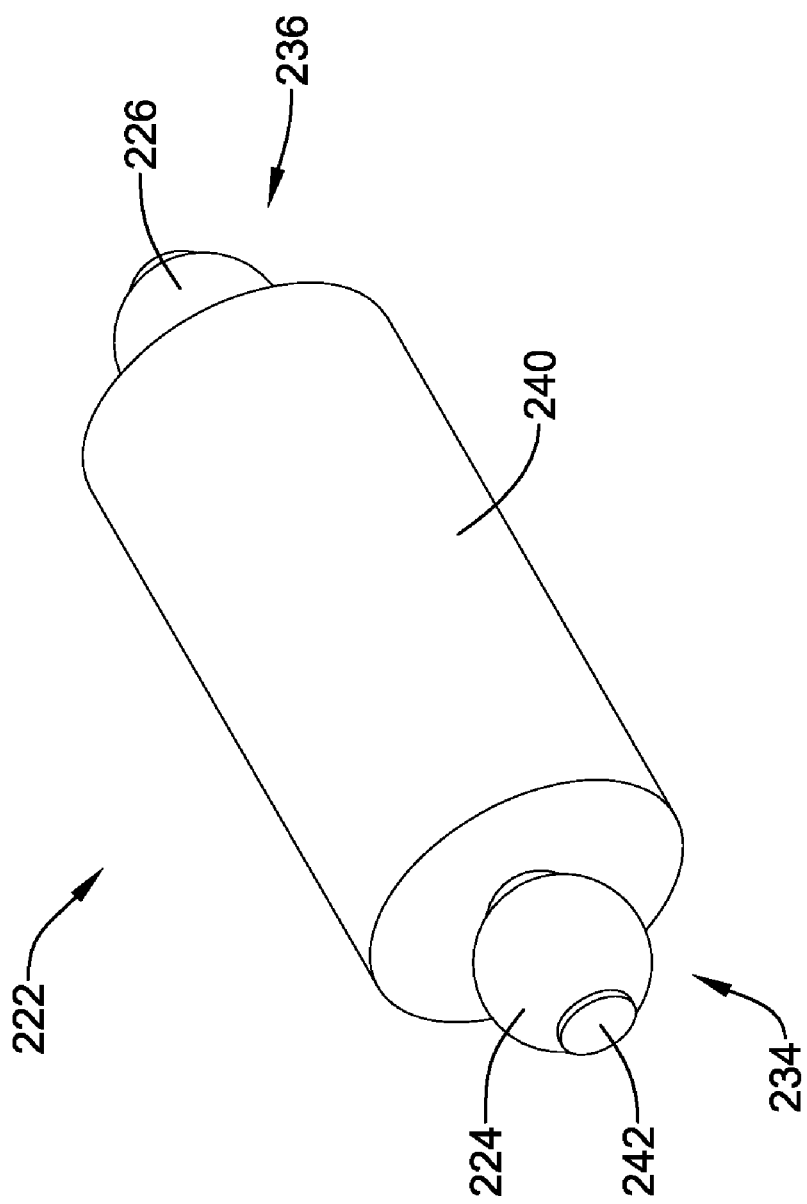
FIG. 8 is a perspective view of another exemplary connector which may be used in stabilizing a vertebral segment.
Figure 9:
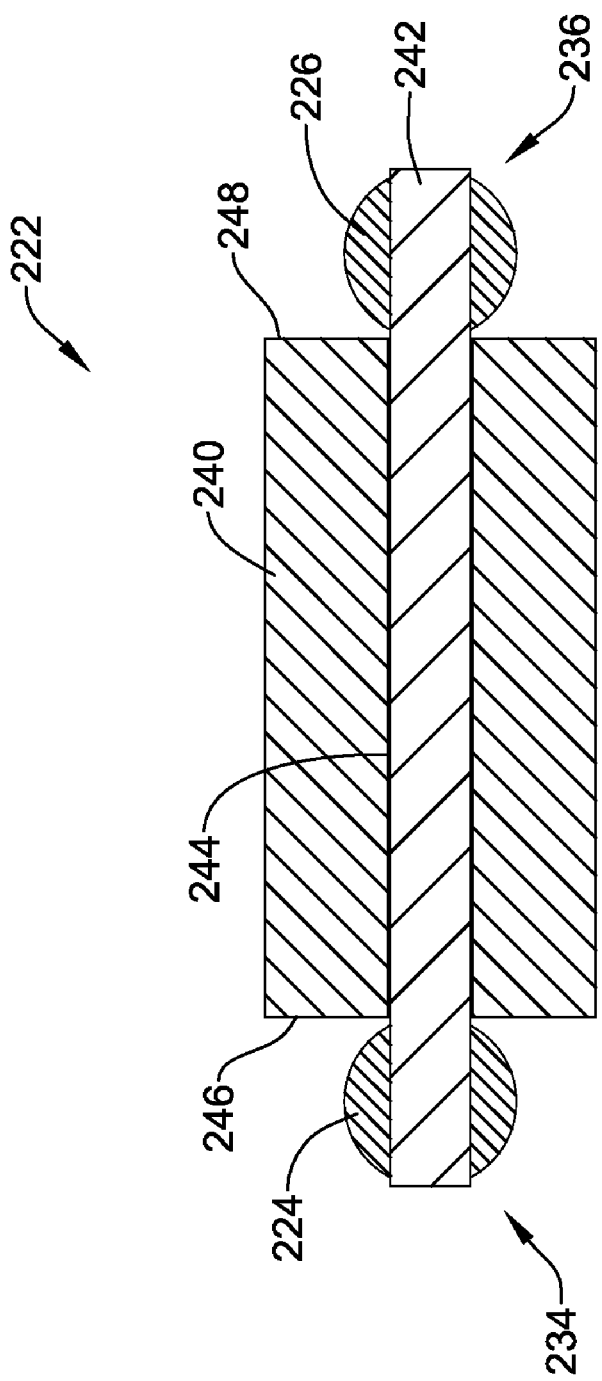
FIG. 9 is a longitudinal cross-sectional view of the connector of FIG. 8.

Another illustrative embodiment of a connector 222 is shown in FIGS. 8 and 9. The connector 222 may be constructed of a plurality of components. For instance, the connector 222 may include a spacer 240, a cord 242 extending through the spacer 240, a first post 224 attached to a first end of the cord 242, and a second post 226 attached to a second end of the cord 242.

In some embodiments, the spacer 240 may be an annular spacer having a lumen 244 extending from a first end 246 of the spacer 240 to a second end 248 of the spacer 240. For example, in some embodiments the spacer 240 may be a cylindrical member having a lumen 244 extending therethrough. In other embodiments, the spacer 240 may be molded, extruded, or otherwise formed over and/or around the cord 242.

The cord 242 may be a single piece of material formed of, for example, a single strand or filament, or the cord 242 may be a multi-filament cord formed of a plurality of strands or filaments. For example, in some embodiments the cord 242 may include a plurality of strands woven, braided, knitted or otherwise intermingled to form the cord 242.

The cord 242 may be formed, at least in part, of an elastomeric material, providing the cord 242 with the ability to be elastically elongated under tension, forming an elongateable member of the connector 222. For instance, in some embodiments, one or more filaments or strands of the cord 242 may be formed of an elastomeric material giving the cord 242 a degree of elasticity. In some instances, one or more elastomeric filaments or strands may be intermingled (e.g., woven, braided, knitted) with one or more inelastic, or relatively more inelastic filaments or strands.

The first post 224, located at the first end 234 of the connector 222, and the second post 226, located at the second end 236 of the connector 222, may be secured to the cord 242. For example, in some embodiments the cord 242 may extend into or through the first post 224 and/or the second post 226. In such embodiments, the first and second posts 224, 226 may be crimped or swaged onto the cord 242. In other embodiments, the first and second posts 224, 226 may be secured to the cord 242 in another fashion. For example, the first and second posts 224, 226 may be melt bonded to, adhesively affixed to, mechanically engaged with, or otherwise secured to the cord 242.

Each of the first post 224 and the second post 226 is illustrated as a substantially spherical ball. However, in other embodiments the first post 224 and/or the second post 226 may be formed to have a different shape, such as a wedge shape, a polygonal shape, or a ovoid shape, if desired.

Figure 10:
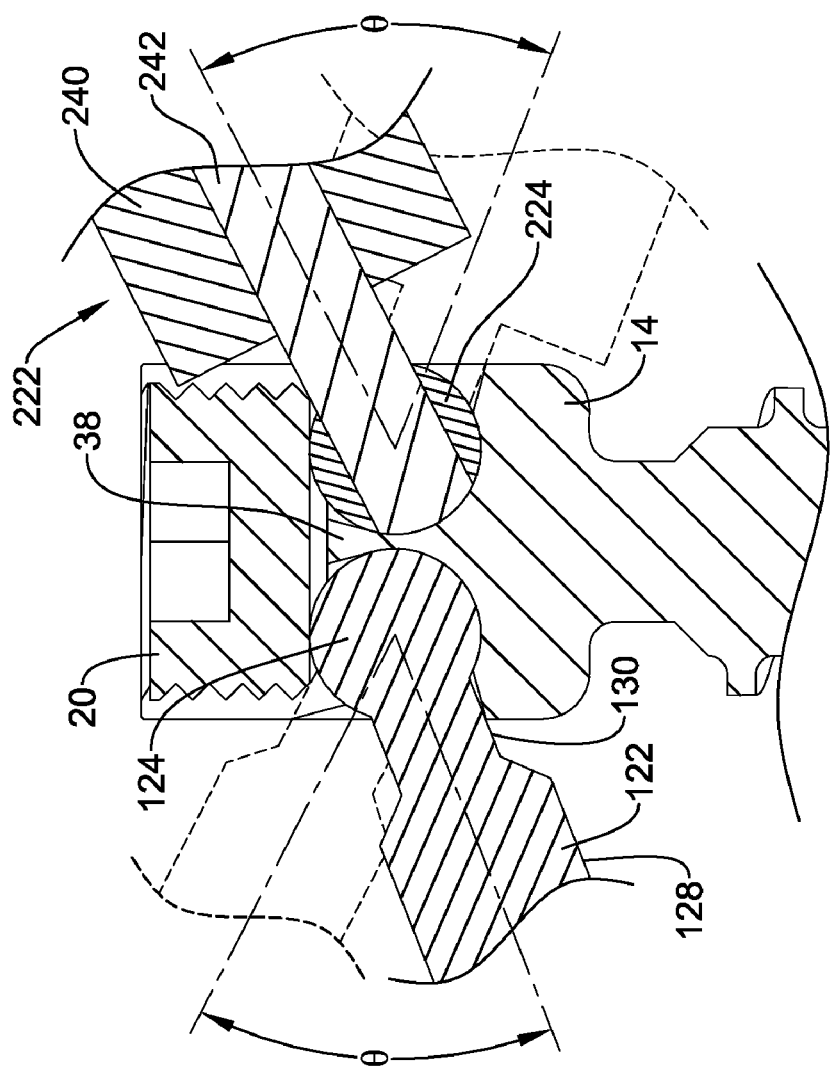
FIG. 10 is a cross-sectional view of the head portion of a vertebral anchor with connectors coupled to the head portion of the vertebral anchor.

FIG. 10 is a cross-sectional view of a head portion 14 of a vertebral anchor 12 having connectors 22 connected thereto. As shown in FIG. 10 the head portion 14 includes a connector 122 extending from a first side of the head portion 14 and a connector 222 extending from a second side of the head portion 14 opposite the first side. Although FIG. 10 illustrates the head portion 14 being coupled to both the connector 122 and the connector 222, in some embodiments the head portion 14 may be coupled to two connectors 122, two connectors 222, or one or more other types of connectors. In some embodiments, the head portion 14 may only be coupled to a single connector. The connector 122 is shown with the post 124 positioned in the first socket 40 of the head portion 14, and the connector 222 is shown with the post 224 positioned in the second socket 42 of the head portion 14.

As shown in FIG. 10, the spherical surface of the post 124 may approximate the spherical surface of the first socket 40, and the spherical surface of the post 224 may approximate the spherical surface of the second socket 42. With the post 124 of the connector 122 positioned in the first socket 40, a portion of the connector 122 may pass through the first side opening 30, connecting a portion of the connector 122 located exterior of the head portion 14 with the post 124. For example, the neck 130 of the connector 122 may extend through the first side opening 30 such that the central portion 128 of the connector 122 is located exterior of the head portion 14 while the post 124 is positioned in the first socket 40 of the head portion 14 of the vertebral anchor 12. Similarly, with the post 224 of the connector 222 positioned in the second socket 42, a portion of the connector 222 may pass through the second side opening 34, connecting a portion of the connector 222 located exterior of the head portion 14 with the post 224. For example, the cord 242 of the connector 222 may extend through the second side opening 34 such that the spacer 240 of the connector 222 is located exterior of the head portion 14 while the post 224 is positioned in the second socket 42 of the head portion 14 of the vertebral anchor 12.

The interaction between the connectors 122, 222 and the head portion 14 of the vertebral anchor 12 may allow the connectors 122, 222 to be multi-directionally pivotably oriented relative to the longitudinal axis of the vertebral anchor 12. In some embodiments, the ball-and-socket type joint formed through the interaction of the post 124, 224 and the socket 40, 42 allows for rotary motion of the connectors 122, 222 relative to the head portion 14 of the vertebral anchor 12 in all directions (i.e., yaw, pitch and roll), or one or more of yaw, pitch and/or roll motions. As used herein, roll is intended to describe rotational movement of the posts 124, 224 relative to the sockets 40, 42, respectively, about an x-axis of a coordinate system, pitch is intended to describe rotational movement of the posts 124, 224 relative to the sockets 40, 42, respectively, about a y-axis of the coordinate system, and yaw is intended to describe rotational movement of the posts 124, 224 relative to the sockets 40, 42, respectively, about a z-axis of the coordinate system.

The connectors 122, 222 may have any desired range of angular motion relative to the head portion 14 of the vertebral anchor 12. For example, the connectors 122, 222 may be able to be pivoted through about 0° to about 120°, about 10° to about 120°, about 30° to about 90°, or about 30° to about 60° of angular motion, in some instances. In some embodiments, the shape and/or size of the side openings 30, 34 may limit the range of pivotable motion of the connectors 122, 222. For example, in some embodiments a portion of the connector 122, 222 may contact a surface of the side openings 30, 34 at one or more extents of the range of motion of the connectors 122, 222.

The threaded fastener 20 of the vertebral anchor 12 may be used to secure the first connector 122 and the second connector 222 to the head portion 14 of the vertebral anchor 12. The threaded fastener 20 may be configured and sized to extend across a portion of the first socket 40 and extend across a portion of the second socket 42. The threaded fastener 20 may span across the partition 38 between the first socket 40 and the second socket 42. When threaded into the threaded opening 28 of the head portion 14, the threaded fastener 20 may engage both the post 124 of the first connector 122 and the post 224 of the second connector 222. When the threaded fastener 20 is sufficiently tightened against the posts 124, 224, the applied force on the posts 124, 224 may prevent further pivoting movement of the connectors 122, 222 relative to the head portion 14, locking the connectors 122, 222 in a singular fixed orientation relative to the head portion 14.

Figure 11:
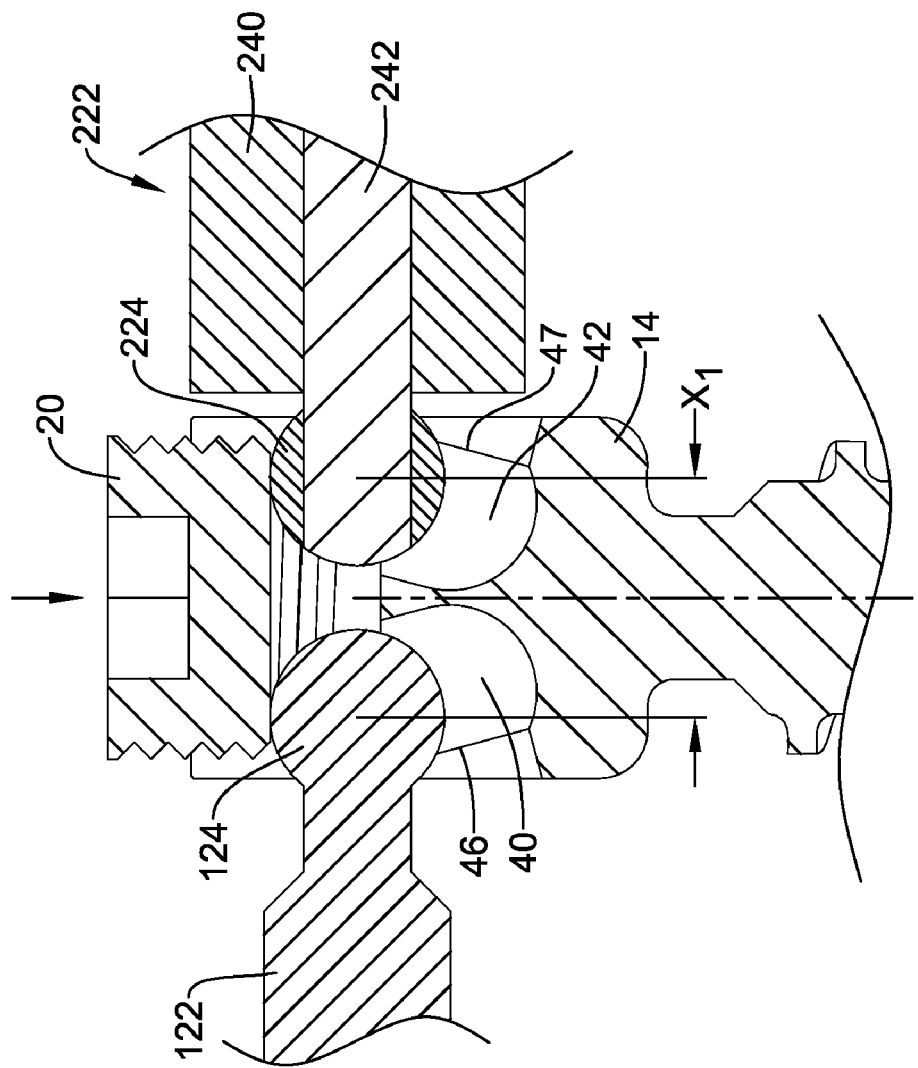
FIGS. 11 and 12 are cross-sectional views of the head portion of a vertebral anchor illustrating the interaction of connectors with the vertebral anchor.
Figure 12:
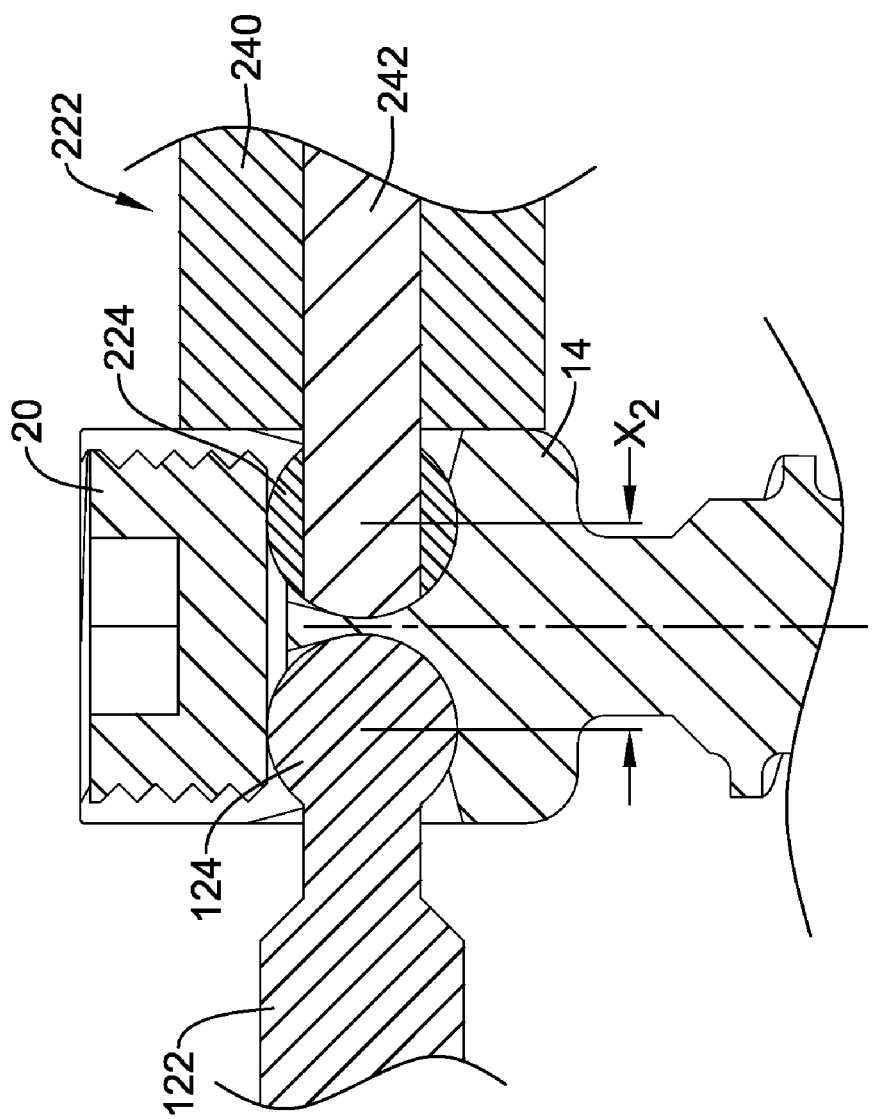

FIGS. 11 and 12 illustrate engagement of the connectors 122, 222 with the head portion 14 of the vertebral anchor 12. The posts 124, 224 of the connectors 122, 222 may initially be inserted into the first and second sockets 40, 42, respectively, in a top loading fashion (i.e., through translation of the posts 124, 224 in a direction generally parallel to the longitudinal axis of the vertebral anchor 12). In other words, the posts 124, 224 of the connectors 122, 222 may initially be inserted into the first and second sockets 40, 42, respectively, by passing the posts 124, 224 through the threaded opening 28 from the upper surface 58 of the head portion 14 of the vertebral anchor 12.

With the posts 124, 224 positioned in the first and second sockets 40, 42, the threaded fastener 20 may be threaded into the threaded opening 28 of the head portion 14. The threaded engagement of the external threads of the threaded fastener 20 with the internal threads of the threaded opening 28 allow the threaded fastener 20 to be translated along the longitudinal axis of the vertebral anchor 12 as the threaded fastener 20 is being rotated with a tool. Rotation of the threaded fastener 20 results in a contact surface of the threaded fastener 20 contacting the posts 124, 224. Rotation of the threaded fastener 20 reduces the volume of the first socket 40 and reduces the volume of the second socket 42, urging the posts 124, 224 further downward into the sockets 40, 42.

Prior to the threaded fastener 20 being fully tightened down onto the posts 124, 224 of the connectors 122, 222, the post 124 may be spaced from the post 224 by a first distance. As shown in FIG. 11, the center of the post 124 may be spaced from the center of the post 224 by a distance $X_1$. As the threaded fastener 20 is rotated and further exerts a force onto the posts 124, 224, the post 124 may slide along the tapered wall 46 of the first socket 40. For instance, the convex surface of the post 124 may contact and slide along the concave surface of the tapered wall 46. Furthermore, as the threaded fastener 20 is rotated and further exerts a force onto the posts 124, 224, the post 224 may slide along the tapered wall 47 of the second socket 42. For instance, the convex surface of the post 224 may contact and slide along the concave surface of the tapered wall 47.

As the posts 124, 224 slide along the tapered walls 46, 47, respectively, the distance between the posts 124, 224 may decrease. For instance, as shown in FIG. 12, as the posts 124, 224 are urged further downward into the sockets 40, 42 by rotation of the threaded fastener 20, the post 124 of the first connector 122 may be drawn toward the longitudinal axis of the vertebral anchor 12 and/or the post 224 of the second connector 222 may be drawn toward the longitudinal axis of the vertebral anchor 12. Thus, the post 124 of the first connector 122 may be drawn toward the post 224 of the second connector 222 and/or the post 224 of the second connector 222 may be drawn toward the post 124 of the first connector 122. As shown in FIG. 12, as the threaded fastener 20 is tightened down on the posts 124, 224 positioned in the sockets 40, 42, the distance between the posts 124, 224 decreases such that the center of the post 124 may be spaced from the center of the post 224 by a distance $X_2$, less than the distance $X_1$. Thus, it can be seen that axial translation of the threaded fastener 20 along the longitudinal axis of the vertebral anchor 12 through rotation of the threaded fastener 20 results in the post 124 of the first connector 122 moving toward the post 224 of the second connector 222 and/or the post 224 of the second connector 222 moving toward the post 124 of the first connector 122. Movement of the posts 124, 224 may be in a direction different from the direction of translational movement of the threaded fastener 20 along the longitudinal axis of the vertebral anchor 12.

Figure 13:
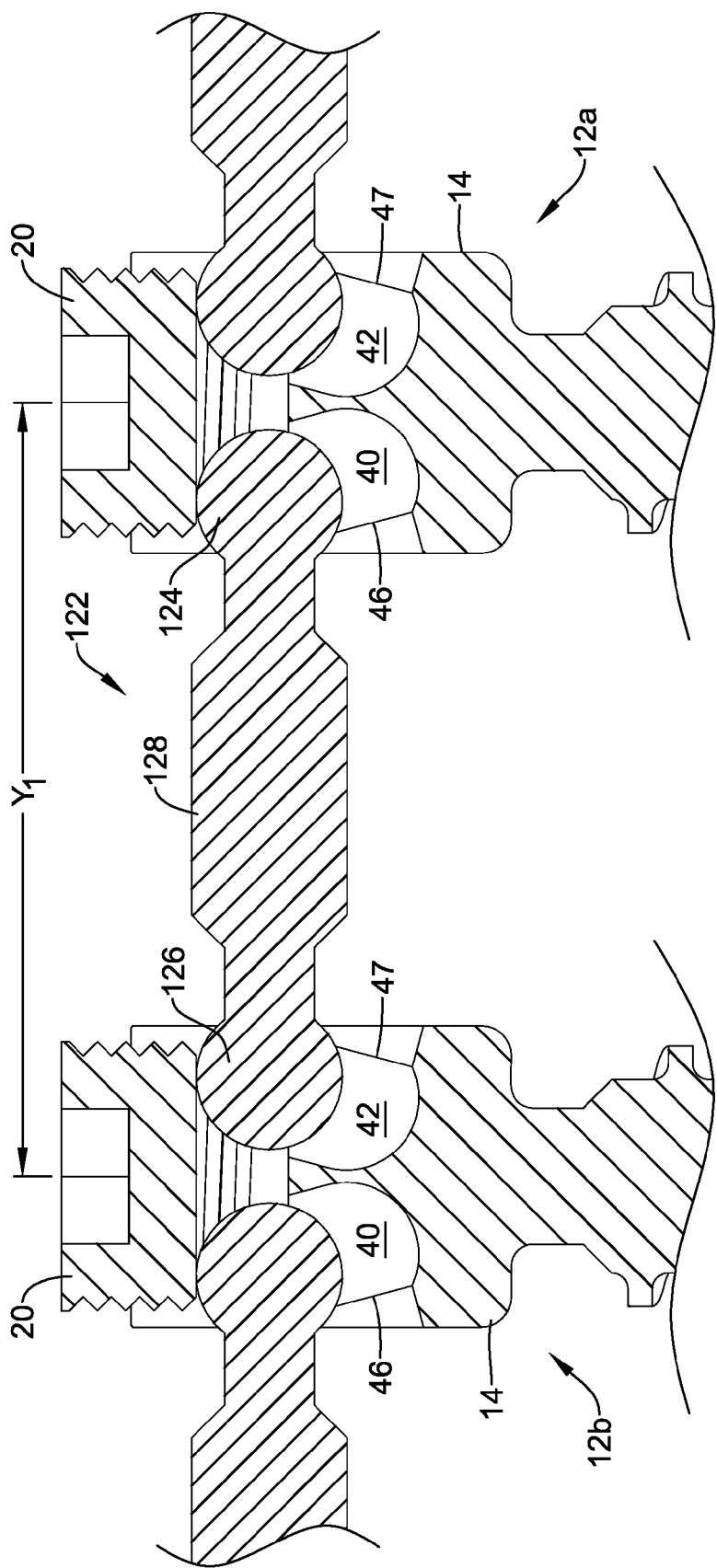
FIGS. 13 and 14 are cross-sectional views of a connector coupled to first and second vertebral anchors illustrating the interaction of the connector with the vertebral anchors.
Figure 14:
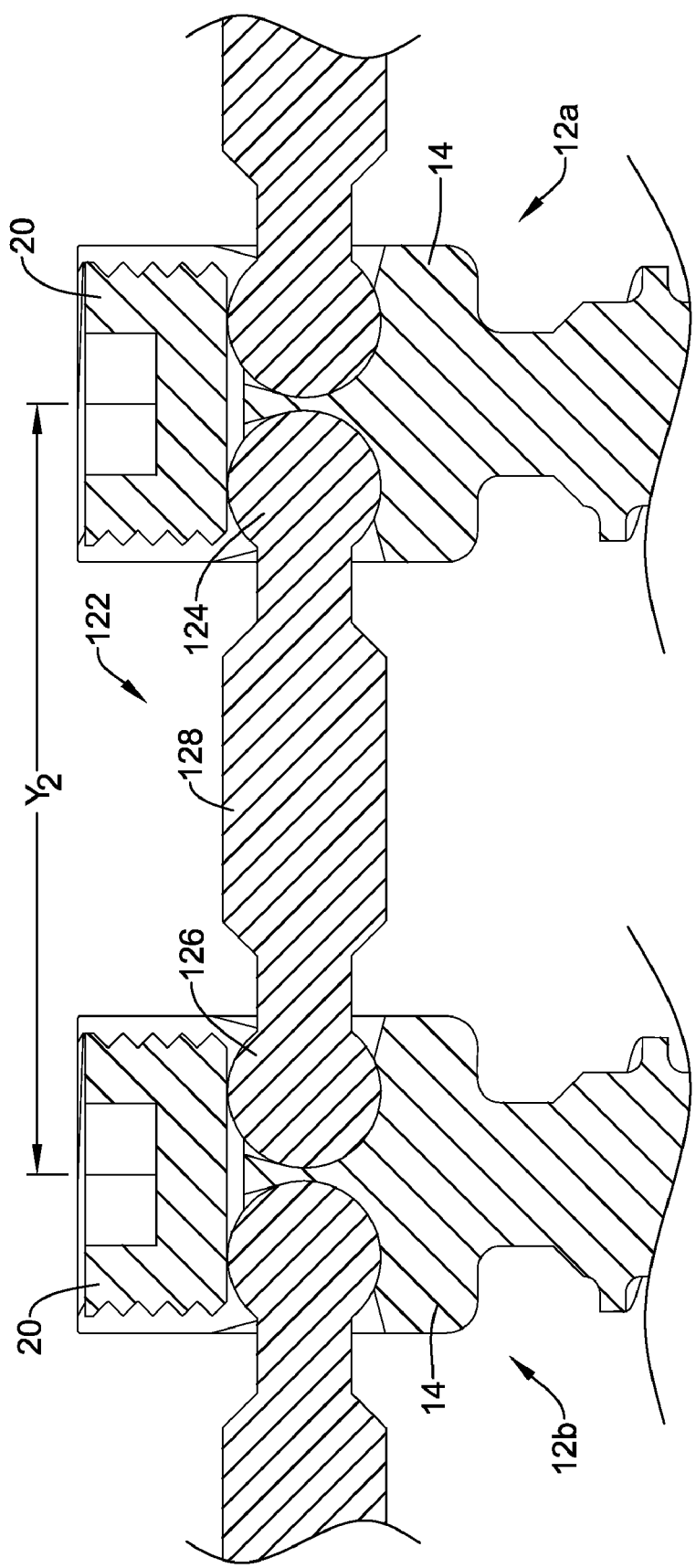

FIGS. 13 and 14 illustrate one possible interaction of a connector 122 with a first vertebral anchor 12a and a second vertebral anchor 12b. The connector 122 may be assembled into the head portions 14 of the first vertebral anchor 12a and the second vertebral anchor 12b in a manner similar to that described above regarding FIGS. 11 and 12. For example, the first post 124 of the connector 122 may be inserted into the first socket 40 of the first vertebral anchor 12a in a top loading manner (i.e., by advancing the post 124 through the threaded opening 28 and into the first socket 40). The second post 126 of the connector 122, likewise, may be inserted into the second socket 42 of the second vertebral anchor 12b in a top loading manner (i.e., by advancing the post 126 through the threaded opening 28 and into the second socket 42).

As shown in FIGS. 13 and 14, as the threaded fastener 20 is tightened down on the post 124 and the threaded fastener 20 is tightened down on the post 126, the distance between the longitudinal axis of the first vertebral anchor 12a and the second vertebral anchor 12b may decrease from a first distance $Y_1$ to a second distance $Y_2$. This may be due, at least in part, to the non-distensible or inelastic nature of the connector 122. As the distance between the first post 124 and the second post 126 may remain substantially unchanged as the threaded fasteners 20 are tightened down on the posts 124, 126, tightening the threaded fasteners 20 draws the first vertebral anchor 12a closer to the second vertebral anchor 12b as the first and second posts 124, 126 slide along the tapered surfaces 46, 47 of the sockets 40, 42, respectively. Such an application of the vertebral anchors 12 and the connector 122 may provide compression to a spinal segment in some situations. Although the connector 122 is illustrated in FIGS. 13 and 14 to demonstrate such a result, it is noted that in some embodiments the usage of the connector 222 may achieve a similar result depending on the elasticity of the cord 242.

Figure 15:
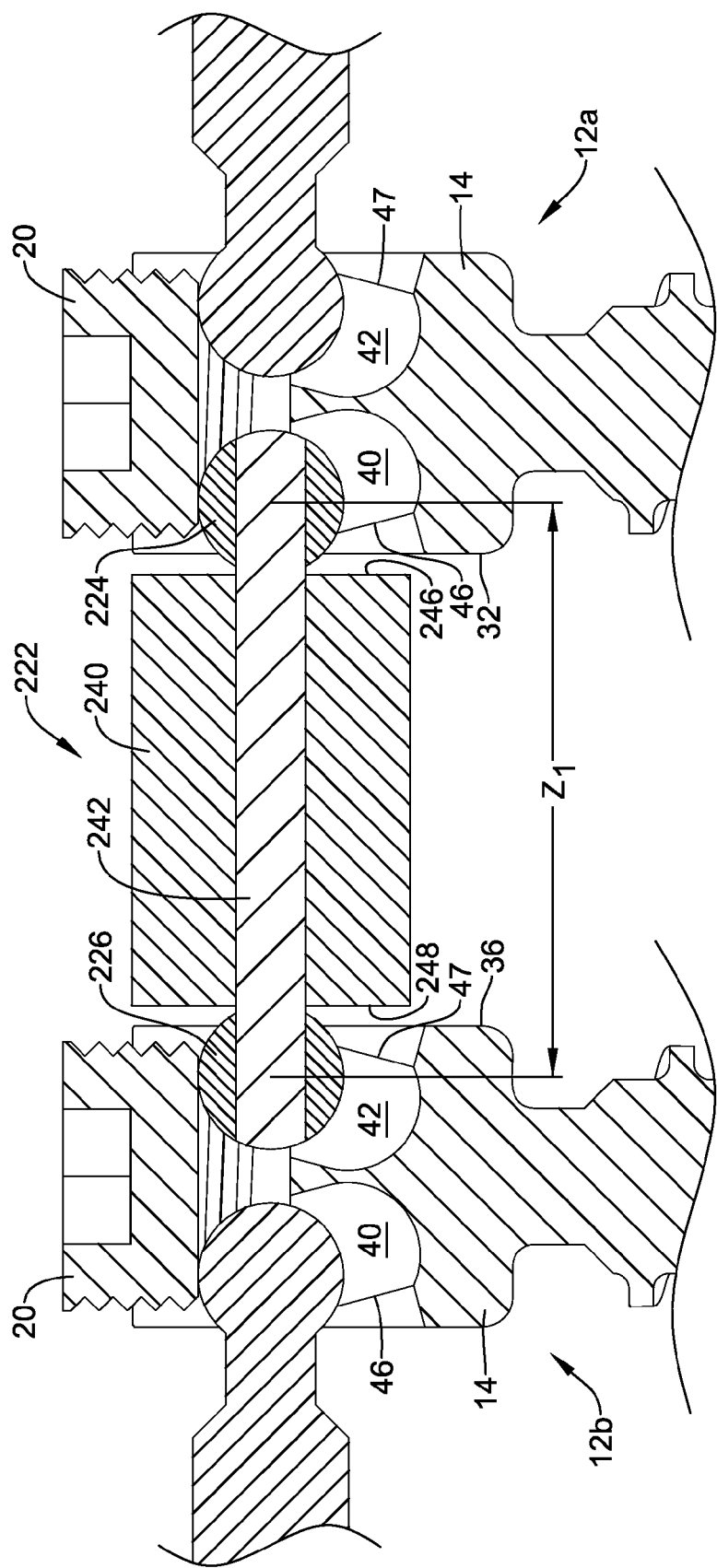
FIGS. 15 and 16 are cross-sectional views of a connector coupled to first and second vertebral anchors illustrating the interaction of the connector with the vertebral anchors.
Figure 16:
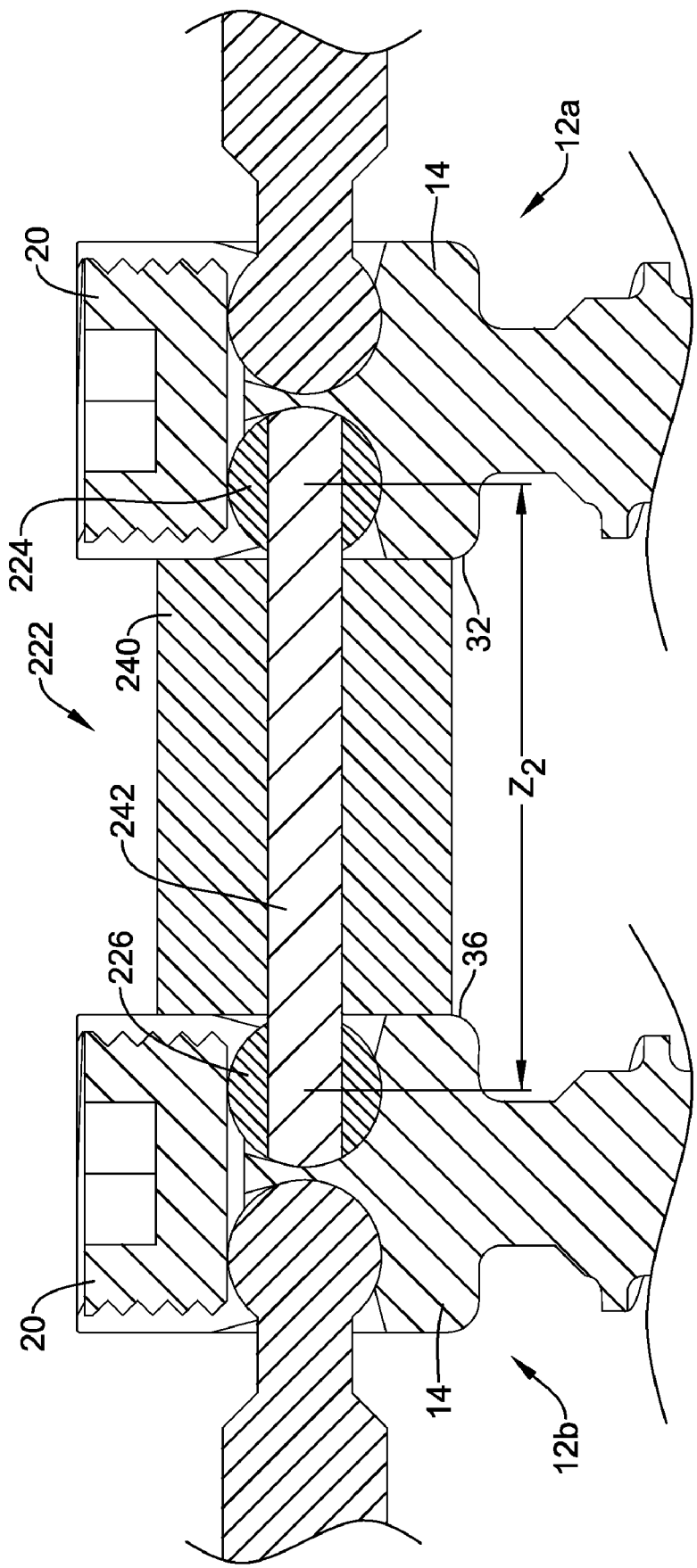

FIGS. 15 and 16 illustrate another possible interaction of a connector 222 with a first vertebral anchor 12a and a second vertebral anchor 12b. The connector 222 may be assembled into the head portions 14 of the first vertebral anchor 12a and the second vertebral anchor 12b in a manner similar to that described above regarding FIGS. 11 and 12. For example, the first post 224 of the connector 222 may be inserted into the first socket 40 of the first vertebral anchor 12a in a top loading manner (i.e., by advancing the post 224 through the threaded opening 28 and into the first socket 40). The second post 226 of the connector 222, likewise, may be inserted into the second socket 42 of the second vertebral anchor 12b in a top loading manner (i.e., by advancing the post 226 through the threaded opening 28 and into the second socket 42). The spacer 240 may be positioned between the first vertebral anchor 12a and the second vertebral anchor 12b. In some embodiments the first end 246 of the spacer 240 may face and/or abut or otherwise contact the first side surface 32 of the first vertebral anchor 12a and the second end 248 of the spacer 240 may face and/or abut or otherwise contact the second side surface 36 of the second vertebral anchor 12b.

As shown in FIGS. 15 and 16, as the threaded fastener 20 of the first vertebral anchor 12a is tightened down on the post 224 and the threaded fastener 20 of the second vertebral anchor 12b is tightened down on the post 226, the cord 242, extending through the spacer 240, may be tensioned, thus increasing the distance between the center of the first post 224 and the center of the second post 226 from a first distance $Z_1$ to a second distance $Z_2$. This may be due, at least in part, to the elasticity of the cord 242. In some embodiments, the cord 242 may not be tensioned prior to positioning the posts 224, 226 in the sockets 40, 42. In other words, in some embodiments the cord 242 may not be pretensioned prior to coupling the connector 222 between the first vertebral anchor 12a and the second vertebral anchor 12b. As the threaded fasteners 20 are tightened down on the posts 224, 226, tightening the threaded fasteners 20 applies a tensile force to the cord 242 as the first and second posts 224, 226 slide along the tapered surfaces 46, 47 of the sockets 40, 42, respectively, and thus move further apart.

In some embodiments, the angle of the slope of the tapered surfaces 46, 47 may dictate the amount of tension applied to the cord 242. For example, the greater the slope of the tapered surfaces 46, 47, the more tension may be placed on the cord 242. In some embodiments, the angle of the slope of the tapered surfaces 46, 47 may allow the cord 242 to be elongated (and thus tensioned) 1 millimeter or more, 2 millimeters or more, 3 millimeters or more, 4 millimeters or more, 5 millimeters or more, or 6 millimeters or more.

It can be seen that, in some embodiments, the amount of tension placed on the cord 242 may be dictated by and/or proportional to the longitudinal displacement of the threaded fastener 20 as the threaded fastener 20 is rotated (screwed) into the threaded opening 28. For example, the greater the longitudinal displacement of the threaded fastener 20 against the post 224, 226, the further the post 224, 226 slides along the tapered surface 46, 47 of the socket 40, 42, respectively, providing greater tension to the cord 242. Thus, in some embodiments, the tensioning or longitudinal elongation of the cord 242 may be adjusted by rotationally adjusting the threaded fastener 20 of one or both of the vertebral anchors 12. Such adjustment may be made during implantation of the assembly in a patient, or in a subsequent medical procedure, such as a percutaneous or minimally invasive medical procedure.

Additionally, in some embodiments a compressive force may be placed on the spacer 240 by the head portions 14 of the vertebral anchors 12a, 12b as tension is being applied to the cord 242 through tightening of the threaded fasteners 20 into the head portions 14 of the vertebral anchors 12a, 12b. For instance, the first side surface 32 of the first vertebral anchor 12a may press against the first end 246 of the spacer 240 and the second side surface 36 of the second vertebral anchor 12b may press against the second end 248 of the spacer 240 to place the spacer 240 in compression.

Thus, it can be seen that such an embodiment may allow for in situ and/or intra-operative tensioning of the cord 242 of the connector 222 and/or in situ and/or intra-operatively compressing the spacer 240. Such an application of the vertebral anchors 12 and the connector 222 may provide a degree of dynamic stabilization to a spinal segment in some situations. Although the connector 222 is illustrated in FIGS. 15 and 16 to demonstrate such a result, it is noted that in some embodiments the usage of the connector 122 having elastic properties may achieve a similar result. In embodiments in which the connector 122 has elastic properties, the connector 122 may provide a degree of flexible stabilization to a spinal segment.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:
1. A vertebral stabilization assembly comprising:
 a vertebral anchor including a head portion and a bone engagement portion extending from the head portion, the head portion including both a first socket and a second socket, wherein the first socket is separated from the second socket by a partition located between the first socket and the second socket;
 a first stabilization member including a post located at a first end of the first stabilization member;

a second stabilization member including a post located at a first end of the second stabilization member;

wherein the post of the first stabilization member is configured to be positioned in the first socket and the post of the second stabilization member is configured to be positioned in the second socket such that the post of the first stabilization member is separated from the post of the second stabilization member by the partition;

a threaded fastener configured to threadedly engage a threaded opening of the head portion;

wherein when the threaded fastener is threaded into the threaded opening, the threaded fastener engages both the post of the first stabilization member and the post of the second stabilization member.

2. The vertebral stabilization assembly of claim 1, wherein as the threaded fastener is threaded into the threaded opening, the post of the first stabilization member is drawn toward the post of the second stabilization member.

3. The vertebral stabilization assembly of claim 2, wherein the first socket includes a tapered wall, wherein the post of the first stabilization member slides along the tapered wall of the first socket.

4. The vertebral stabilization assembly of claim 3, wherein the second socket includes a tapered wall, wherein the post of the second stabilization member slides along the tapered wall of the second socket.

5. The vertebral stabilization assembly of claim 1, wherein the head portion includes a first opening on a first side of the head portion providing lateral access to the first socket, and the head portion includes a second opening on a second side of the head portion providing lateral access to the second socket.

6. The vertebral stabilization assembly of claim 5, wherein when assembled, a portion of the first stabilization member extends through the first opening, and a portion of the second stabilization member extends through the second opening.

7. The vertebral stabilization assembly of claim 6, wherein when assembled the first stabilization member extends in a first direction from the head portion of the vertebral anchor and the second stabilization member extends in a second direction from the head portion of the vertebral anchor.

8. The vertebral stabilization assembly of claim 1, wherein the bone engaging portion defines a longitudinal axis of the vertebral anchor;

wherein the post of the first stabilization member is positionable into the first socket through translation of the post in a direction generally parallel to the longitudinal axis; and wherein the post of the second stabilization member is positionable into the second socket through translation of the post in a direction generally parallel to the longitudinal axis.

9. The vertebral stabilization assembly of claim 1, wherein a surface of the post of the first stabilization member configured to contact a surface of the first socket is a spherical surface.

10. The vertebral stabilization assembly of claim 9, wherein a surface of the post of the second stabilization member configured to contact a surface of the second socket is a spherical surface.

11. A vertebral anchor comprising:
a head portion;
a shaft portion extending from the head portion and defining a longitudinal axis;
the head portion including a first socket and a second socket;

the head portion further including a first side opening providing access to the first socket from a first side of the head portion;

the head portion further including a second side opening providing access to the second socket from a second side of the head portion;

wherein the first socket includes a first cylindrical bore defining a side wall which tapers toward the longitudinal axis from an upper portion of the first socket toward a lower portion of the first socket, the first cylindrical bore having a first central axis at an oblique angle to the longitudinal axis; and wherein the second socket includes a second cylindrical bore defining a side wall which tapers toward the longitudinal axis from an upper portion of the second socket toward a lower portion of the second socket, the second cylindrical bore having a second central axis at an oblique angle to the longitudinal axis.

12. The vertebral anchor of claim 11, further comprising a threaded fastener configured to threadedly engage with the head portion;

wherein the threaded fastener is configured to extend across a portion of the first socket and extend across a portion of the second socket.

13. The vertebral anchor of claim 12, wherein the head portion includes a partition separating the first socket from the second socket.

14. The vertebral anchor of claim 13, wherein the threaded fastener spans across the partition between the first socket and the second socket.

15. The vertebral anchor of claim 12, wherein the head portion includes a threaded opening in communication with both the first socket and the second socket.

16. The vertebral anchor of claim 15, wherein the first socket has a volume and the second socket has a volume;

wherein rotation of the threaded fastener in the threaded opening reduces the volume of the first socket and reduces the volume of the second socket.

17. A method of stabilizing a vertebral segment, the method comprising:

securing a vertebral anchor to a vertebra, the vertebral anchor including a head portion and a shaft portion extending from the head portion, the head portion including a first socket and a second socket, the shaft portion defining a longitudinal axis;

wherein the first socket includes a first cylindrical bore defining a first central axis at an oblique angle to the longitudinal axis;

wherein the second socket includes a second cylindrical bore defining a second central axis at an oblique angle to the longitudinal axis;

positioning a post of a first stabilization member in the first socket;

positioning a post of a second stabilization member in the second socket;

with a single fastener, securing the post of the first stabilization member in the first socket and securing the post of the second stabilization member in the second socket;

wherein during the securing step, the post of the first stabilization member moves toward the post of the second stabilization member.

18. The method of claim 17, wherein the vertebral anchor is a first vertebral anchor; and wherein the first stabilization member extends from a second vertebral anchor to the first vertebral anchor and the second stabilization member extends from a third vertebral anchor to the first vertebral anchor.

19. The method of claim 18, wherein the first stabilization member includes an elongate member extending through a spacer.

20. The method of claim 19, wherein during the securing step, the elongate member is placed in tension and the spacer is placed in compression.

21. The method of claim 20, wherein, prior to the securing step, the elongate member is not in tension.

22. The method of claim 19, wherein the second stabilization member is a rigid member.

23. The method of claim 18, wherein during the securing step, the second vertebral anchor is drawn closer to the first vertebral anchor.

24. The method of claim 18, wherein during the securing step the first stabilization member is tensioned between the first vertebral anchor and the second vertebral anchor.

25. The method of claim 17, wherein during the securing step, the post of the first stabilization member slides along a tapered surface of the first socket.

26. The method of claim 25, wherein during the securing step, the post of the second stabilization member slides along a tapered surface of the second socket.

27. The method of claim 26, wherein the tapered surface of the first socket slopes toward the tapered surface of the second socket.

28. The method of claim 17, wherein during the securing step, the fastener is translated in a first direction while the post of the first stabilization member is translated in a second direction, different from the first direction.

29. The method of claim 28, wherein during the securing step, the post of the second stabilization member is translated in a third direction, different from the first direction and the second direction.

* * * * *